(12) United States Patent
Stelmach et al.

(10) Patent No.: US 11,046,153 B1
(45) Date of Patent: Jun. 29, 2021

(54) THREE STAGE AIR PURIFICATION FOR RAIL VEHICLES

(71) Applicant: Knorr Brake Company LLC, Westminster, MD (US)

(72) Inventors: Richard Stelmach, Hanover, PA (US); Justin Jones, Thurmont, MD (US); Tyler Bowie, Westminster, MD (US)

(73) Assignee: Knorr Brake Company, LLC, Westminster, MD (US)

( * ) Notice: Subject to any disclaimer, the term of this patent is extended or adjusted under 35 U.S.C. 154(b) by 0 days.

(21) Appl. No.: 17/195,867

(22) Filed: Mar. 9, 2021

Related U.S. Application Data

(60) Provisional application No. 63/039,622, filed on Jun. 16, 2020.

(51) Int. Cl.
| | | |
|---|---|---|
| *B60H 3/06* | (2006.01) | |
| *B60H 3/00* | (2006.01) | |
| *A61L 9/20* | (2006.01) | |
| *A61L 9/22* | (2006.01) | |

(52) U.S. Cl.
CPC ............. *B60H 3/0608* (2013.01); *A61L 9/20* (2013.01); *A61L 9/22* (2013.01); *B60H 3/0078* (2013.01); *A61L 2209/16* (2013.01)

(58) Field of Classification Search
CPC ............ A61L 9/20; A61L 9/22; B60H 3/0078
See application file for complete search history.

(56) References Cited

U.S. PATENT DOCUMENTS

| | | | |
|---|---|---|---|
| 7,655,076 B2 | 2/2010 | Griffiths et al. | |
| 2008/0170971 A1* | 7/2008 | Bergeron | ................ B03C 3/016 422/171 |

* cited by examiner

*Primary Examiner* — Kevin Joyner
(74) *Attorney, Agent, or Firm* — Bond Schoeneck and King PLLC; David Nocilly

(57) ABSTRACT

An air purification system for use with rail car HVAC system to remove or destroy harmful pathogens in the air. The air purification system has a housing with an inlet, an outlet, and a passageway extending between the inlet and the outlet. An intense field generator and filter is used to charge any particles in the air and remove them from the air flow. An ultraviolet radiation source is positioned to direct ultraviolet illumination into the passageway. Finally, a dielectric barrier discharge unit having a high voltage electrode coupled to a dielectric barrier and a ground electrode spaced apart from the high voltage electrode is used to form a low temperature plasma chamber is in communication with the passageway so that the ions created in the plasma chamber will attach to and destroy any remaining particles in the air flow.

15 Claims, 11 Drawing Sheets

US 11,046,153 B1

THREE STAGE AIR PURIFICATION FOR RAIL VEHICLES

CROSS-REFERENCE TO RELATED APPLICATIONS

The present application claims priority to U.S. Provisional Application No. 63/039,622, filed on Jun. 16, 2020.

BACKGROUND OF THE INVENTION

1. Field of the Invention

The present invention relates to air treatment systems for rail vehicles and, more specifically, to a heating ventilation and air conditioning (HVAC) system that can reliably eliminate airborne pathogens.

2. Description of the Related Art

The current global COVID-19 pandemic has revealed the need for systems that can address airborne pathogens including viruses. For example, rail vehicles such as those used for public transportation are critical infrastructure that must remain safe to remain open during a pandemic or to be placed back into service after quarantining periods have ended and governments allow reopening. Current cleaning methods, such as ultraviolet (UV) radiation of surfaces can provide significant improvements to reduce spread of contagions, but there is still vast room for improvement. One significant risk point in the use of rail vehicles is the inability of conventional HVAC systems to effectively filter out airborne viruses, including COVID-19.

BRIEF SUMMARY OF THE INVENTION

The present invention provides an air purification system for use with rail car HVAC system that can reliably remove or destroy harmful pathogens. More specifically, the air purification system for a rail car comprises a housing having an inlet, and an outlet, and a passageway extending between the inlet and the outlet. An intense field generator having a series of openings formed therethrough and a series of electrodes, each of which is positioned in one of the series of openings so that a tip of each electrode extends into a center of each opening, is positioned in the passageway so that air flows through the openings. An intense field dielectric filter having a plurality of channels formed therethrough is aligned with the openings of the intense field generator. Each channel is defined by a first surface comprising a first electrode and a second surface opposing the first electric and comprises a second electrode, wherein the first electrode and the second electrode are encompassed by a dielectric material, to generate a corona discharge in the openings and charge any particles in the air flow. An ultraviolet radiation source is positioned to direct ultraviolet illumination into the passageway. A dielectric barrier discharge unit having a high voltage electrode coupled to a dielectric barrier and a ground electrode spaced apart from the high voltage electrode is used to form a low temperature plasma chamber that is in communication with the passageway so that the ions created in the plasma chamber will attach to and destroy any remaining particles in the air flow.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
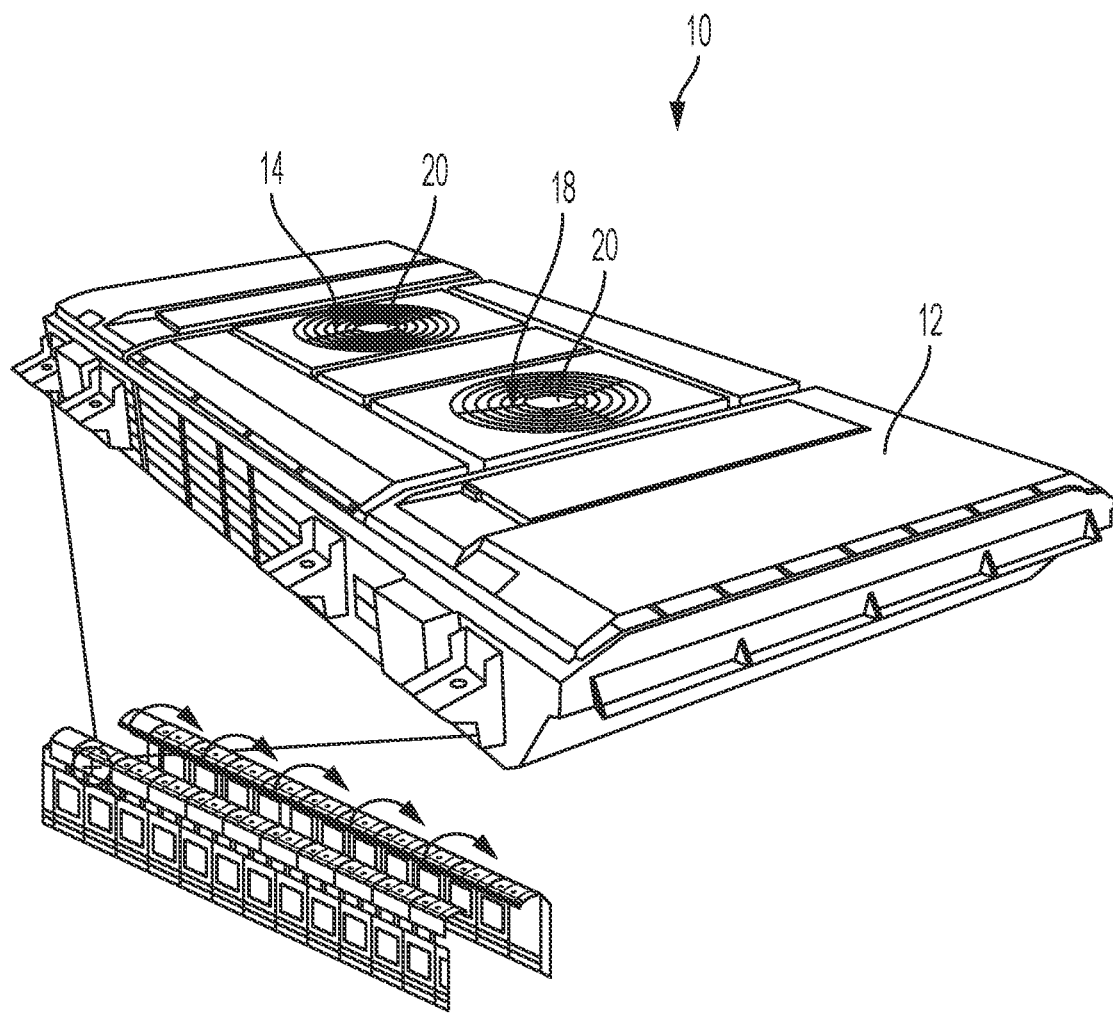
FIG. 1 is a perspective view of an air treatment system for a rail car according to the present invention.

Referring to the figures, wherein like numeral refer to like parts throughout, there is seen in FIG. 1 a rail car air treatment system 10 for eliminating airborne pathogens from a location such as a rail car. Air treatment system 10 generally comprises a housing 12 having an air intake 14 that can withdraw air from the interior of the rail car, an internal air passageway 16 through which air passes and may be treated, and an air outlet 18 for returning purified or treated air to the rail car. Air treatment system 10 includes one or more fans 20 for creating and maintaining a pressure differential along passageway 16 such that air flows into intake 14, through passageway 16, and out of outlet 18 along an air flow pathway 24. It should be recognized that air treatment system 10 may include air conditioning elements such as heat exchangers, heaters, and the like to provide temperature conditioning of air flowing through air treatment system 10. Air treatment system 10 additionally includes one or more power sources 22 that can connect to and transform local power (such as the 24, 37.5, 72, or 110 volt supply available in conventional rail cars) into the appropriate voltage for each element of the air treatment system 10, as explained below.

Figure 2:
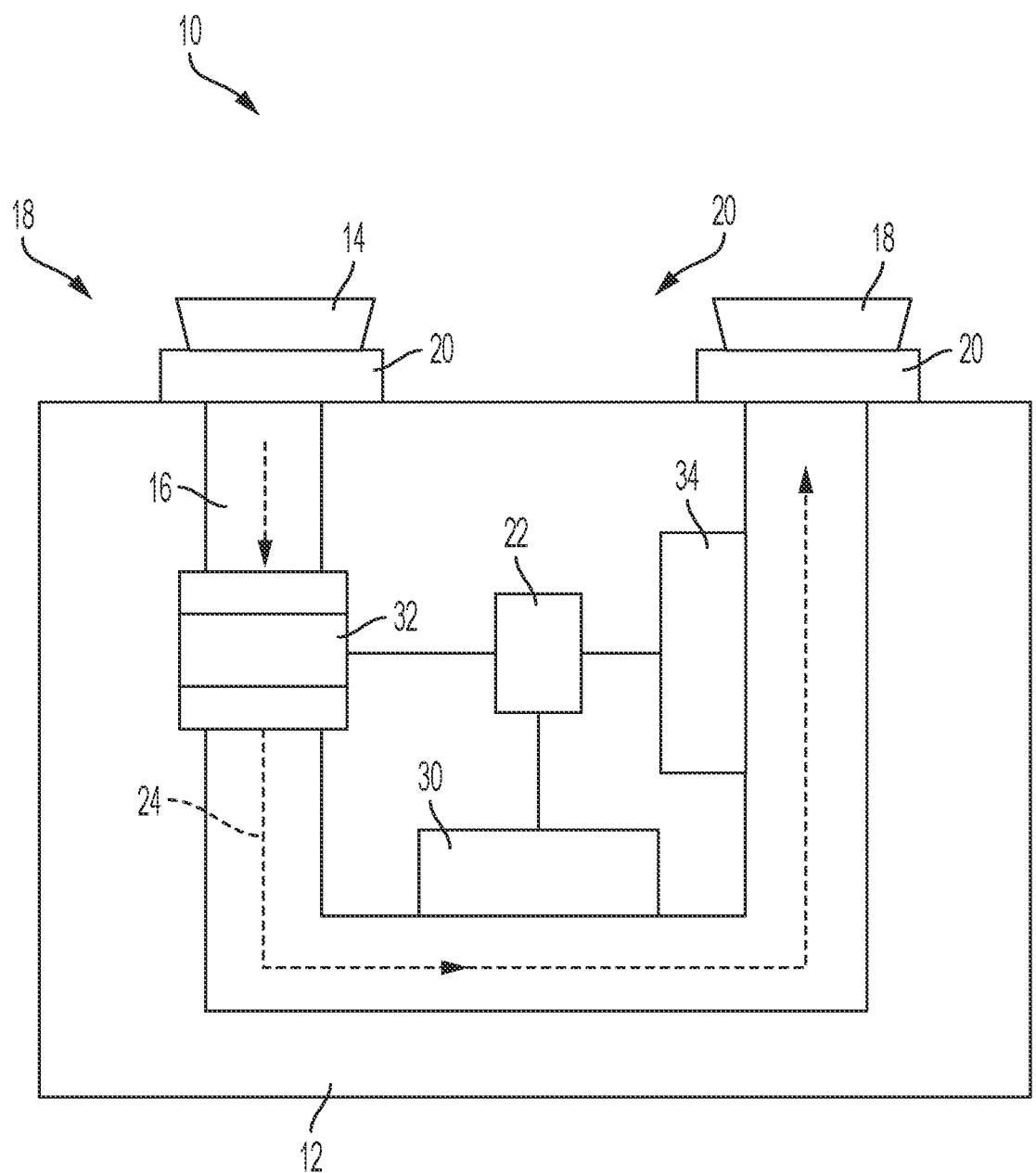
FIG. 2 is a schematic of an air treatment system for a rail car according to the present invention.
Figure 3:
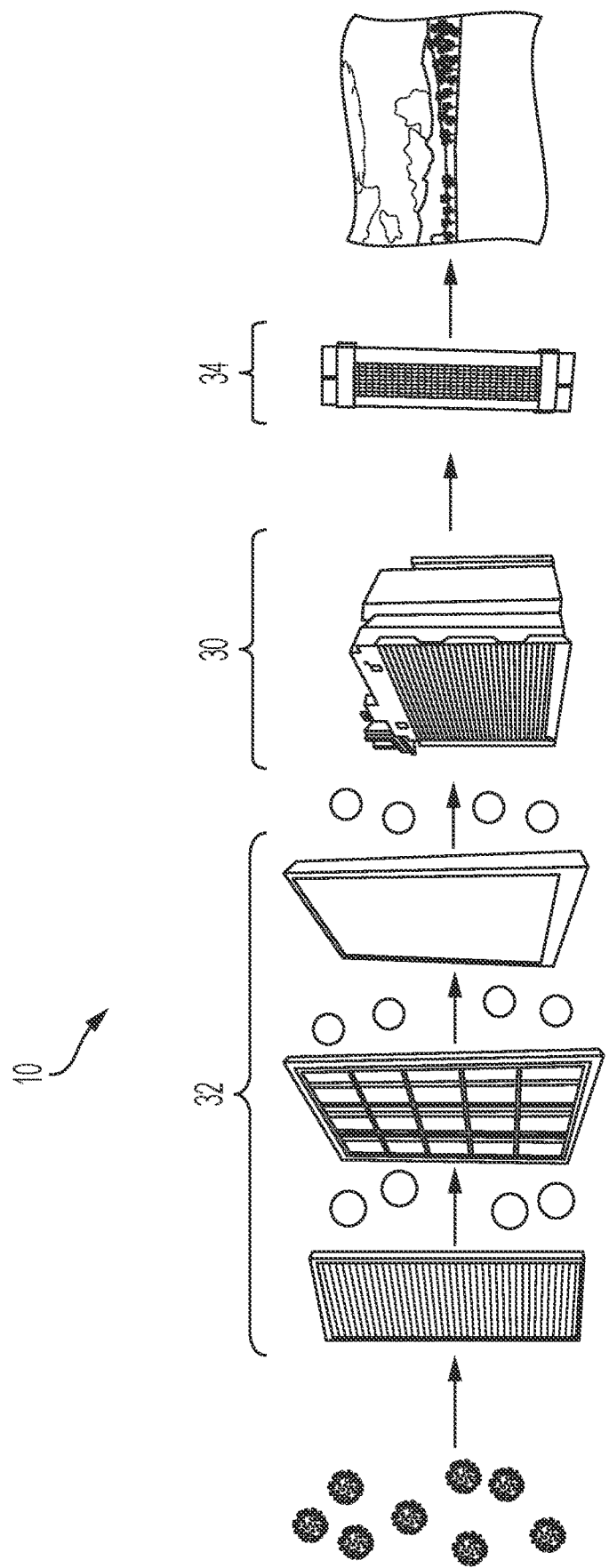
FIG. 3 is a schematic of a three-phase air purification approach for a rail car air treatment system according to the present invention.

Referring to FIGS. 2 and 3, air treatment system 10 has three air purification phases and, as explained, below, each has specific power requirements that may differ from the other phases. Generally, air treatment system 10 includes an intense field dielectric phase 32, an ultraviolet germicidal irradiation phase 30, and a dielectric barrier discharge phase 34 that are positioned in series along passageway 16 and, in combination, can purify air passing through air treatment system 10 to remove contaminants, including biological hazards such as bacterial and viruses, as well as small particulate matter and chemical pollutants. The combination of ultraviolet germicidal irradiation phase 30 along with intense field dielectric phase 32 and a dielectric barrier discharge phase 34 synergistically ensure that any pathogens, including viruses, are inactivated or filtered out, thereby providing a significant safety improvement over conventional systems that rely on single purification phases such as UVC irradiation and allowing for continuous use when a rail car is in service with high throughput.

Figure 4:
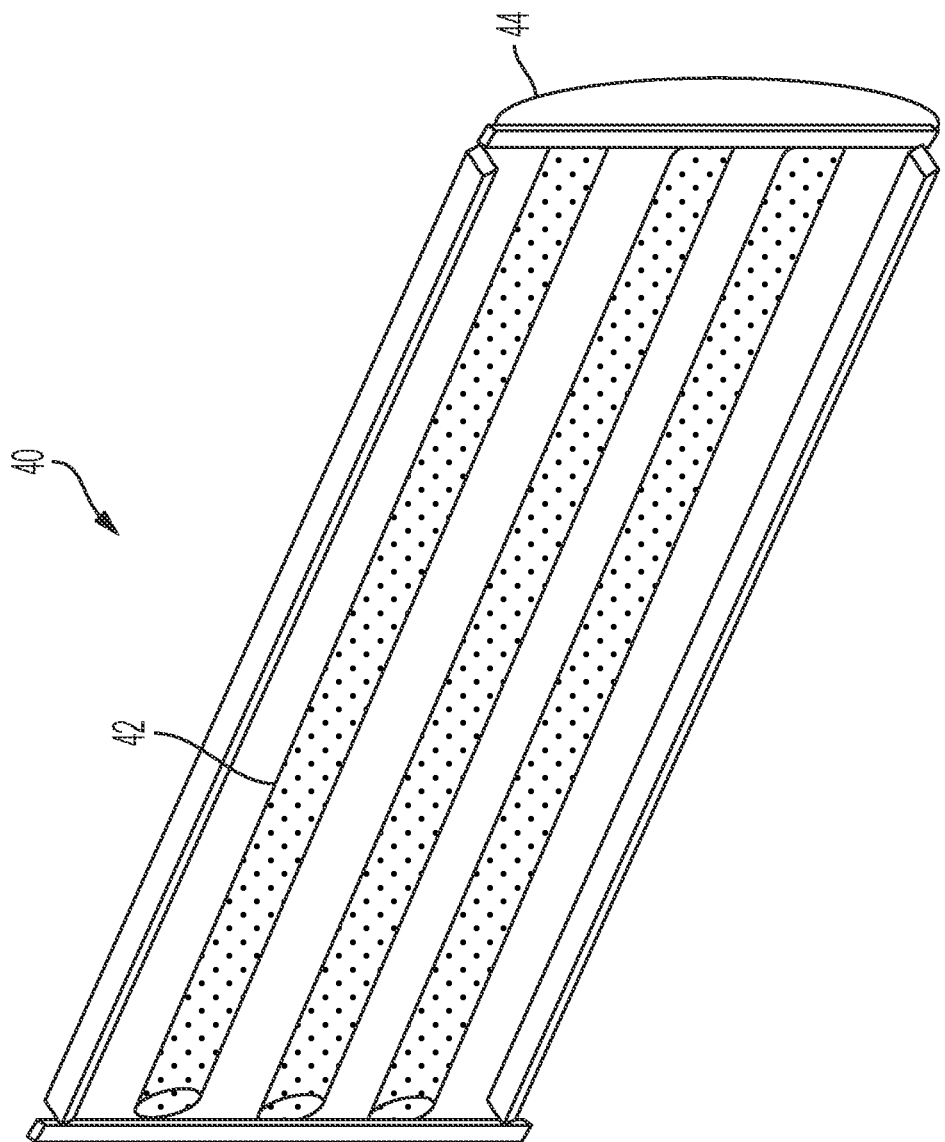
FIG. 4 is a schematic of an ultraviolet germicidal irradiation phase for a rail car air treatment system according to the present invention.

Referring to FIG. 4, intense field dielectric phase 32 of air treatment system 10 is positioned transversely across passageway 16 so that air flow in passageway 16 must flow through intense field dielectric phase 32. Intense field dielectric phase 32 comprises a prefilter 50, a field generator 52, and intense field dielectric filter 54 that are aligned for treatment of air in passageway 16 as it flows therethrough.

Prefilter 50 comprises a conventional filtration panel having low resistance that can filter out particles having a size between 1 and 2 millimeters. Prefilter 50 is therefore intended to remove large airborne particles and debris from the air flow. Prefilter 50 is preferably washable for reuse and manufactured from materials that provide a long service life. The pre-filter 50 can be made of a nylon material or be a traditional paper type filter.

Figure 5:
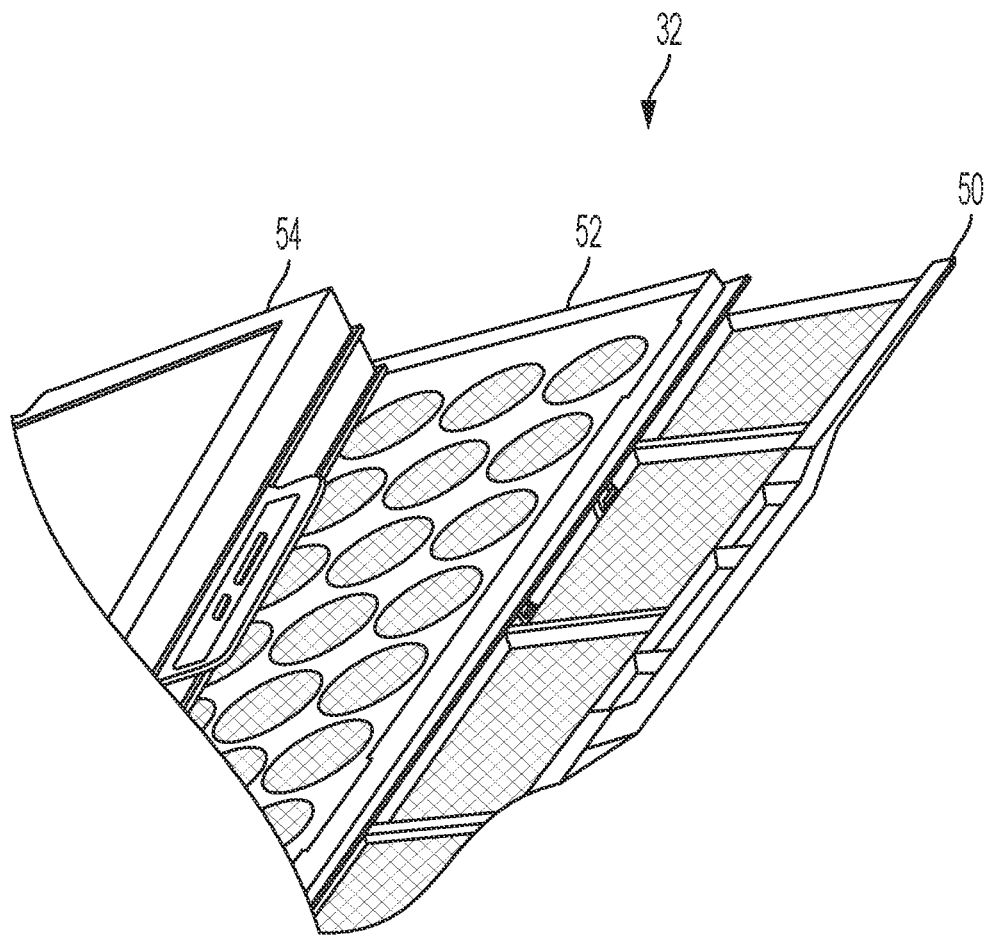
FIG. 5 is a schematic of an intense field dielectric phase of a rail car air treatment system according to the present invention.

Referring to FIG. 5, field generator 52 comprises a thin metal plate 56 having a series of circular holes 58 extending through plate 56 and positioned in an array about the major surfaces of plate 56. A pin electrode 60 is positioned so that its tip 62 is located in the middle of each hole 58. The application of a voltage between the tip 62 of pin electrode 60 and the edge of hole 58 creates an effect referred to as a corona discharge 64 within the holes 58. As airborne particles in the air flowing through passageway 16 pass through the corona discharge 64 formed in hole 58, the airborne particles will become charged. The electrode 60 is between 0-50 mm from the edge of the hole 58. The field generator 52 transforms 24 volts of direct current (VDC) input to the 8000 VDC used to create the corona discharge.

Figure 6:
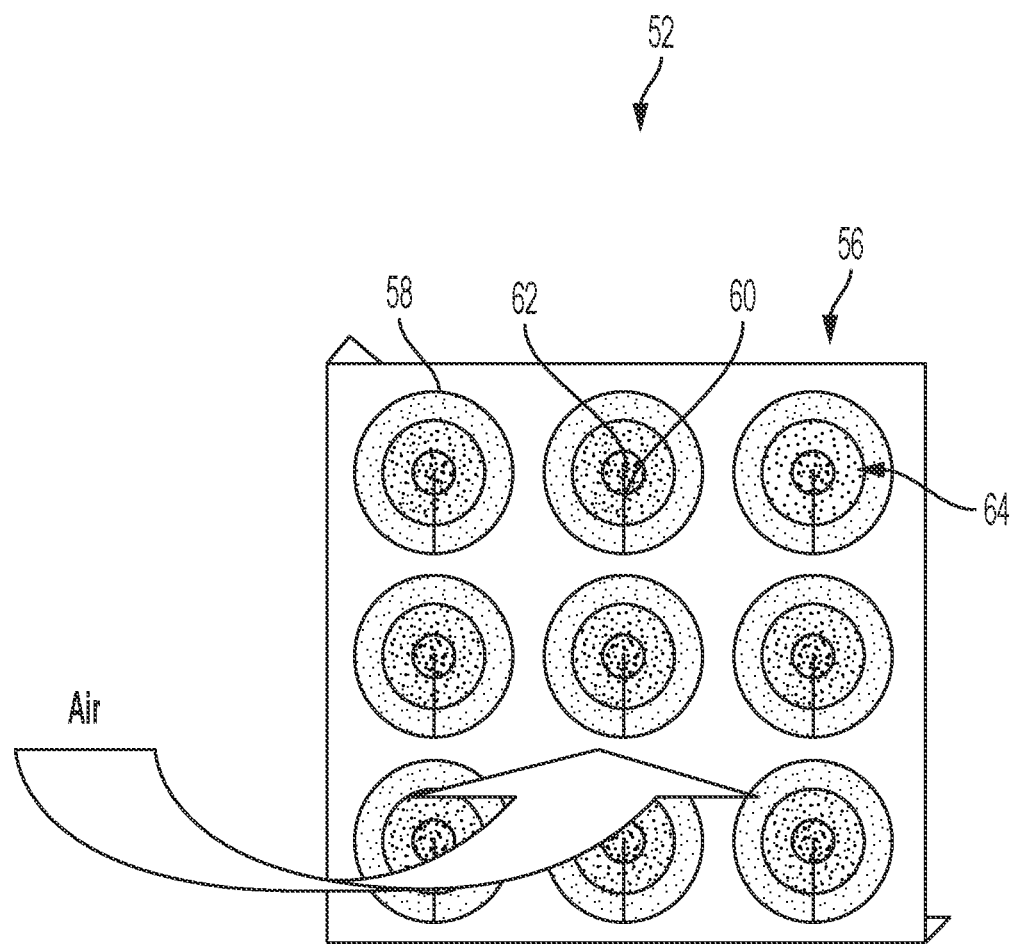
FIG. 6 is a schematic of an intense field dielectric generator according to the present invention.
Figure 7:
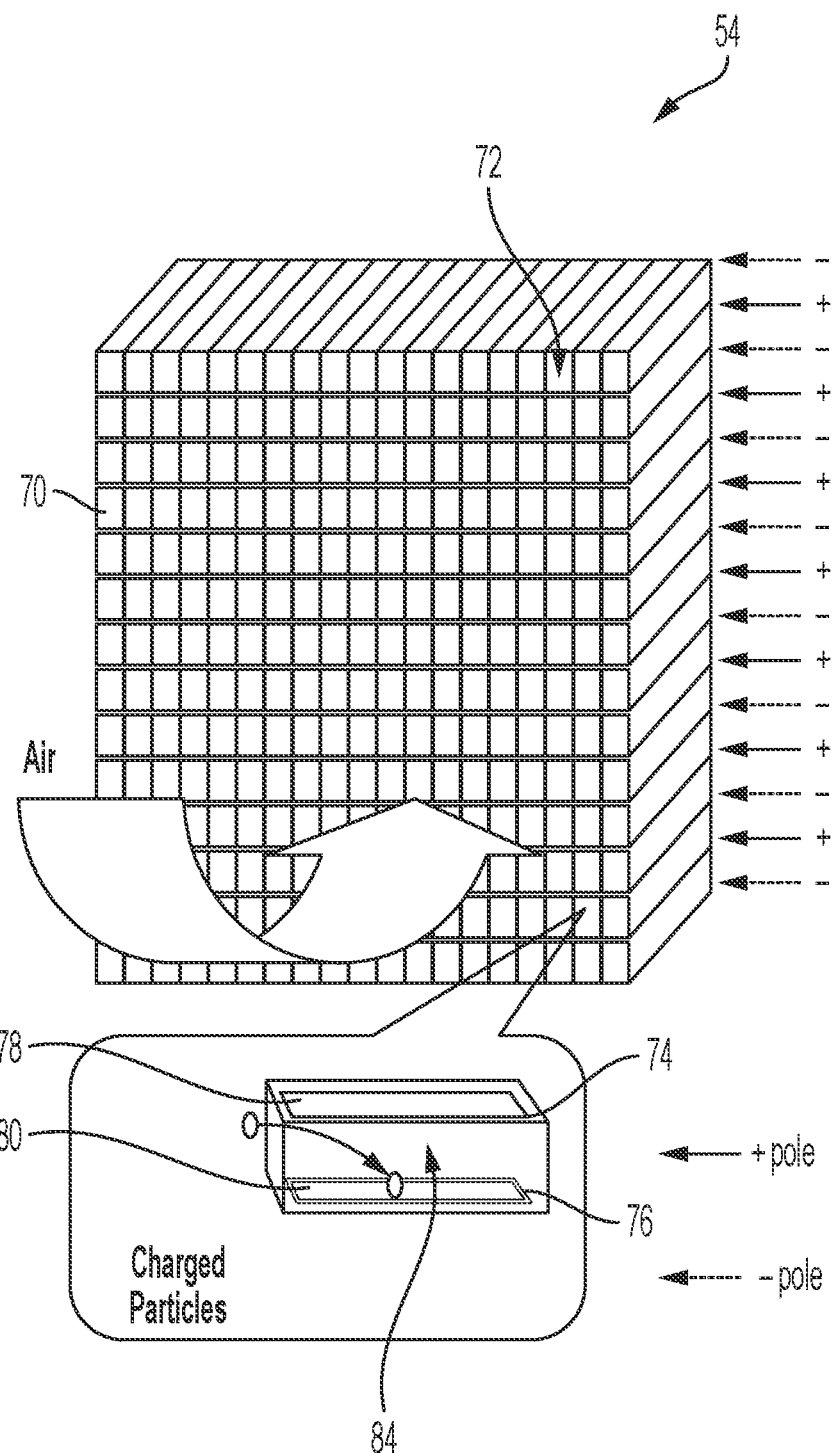
FIG. 7 is a schematic of an intense field dielectric filter according to the present invention.
Figure 8:
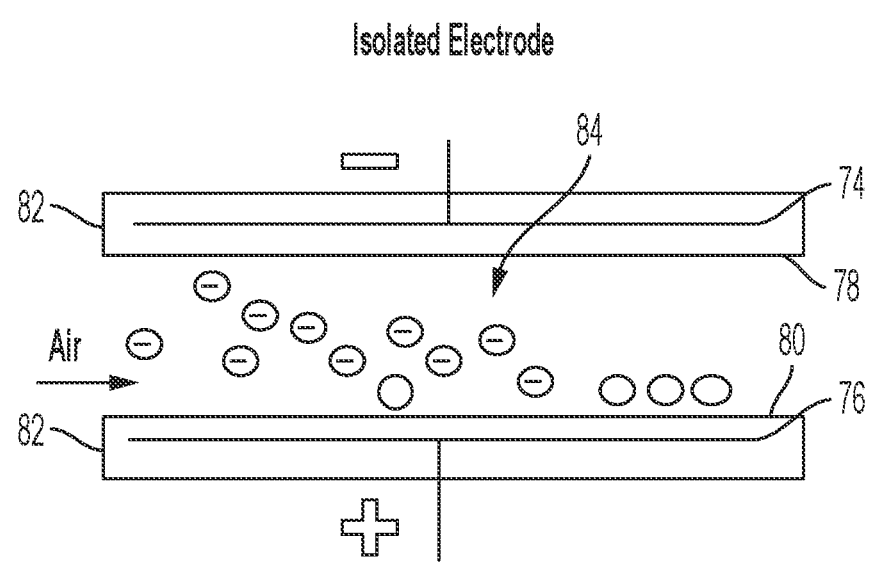
FIG. 8 is a schematic of a microchannel of an intense field dielectric filter according to the present invention.

Referring to FIG. 6, intense field dielectric filter 54 comprises a grid 70 defining a plurality of microchannels 72. Grid 70 is positioned proximately to field generator and aligned therewith so that air flowing through holes 58 of field generator 52 will pass through microchannels 72. Microchannels 72 may have cross-sectional dimensions of approximately 3 mm by 1.2 to 1.5 mm or 3 mm by 1.7 to 2 mm. The depth of the microchannels 72 may vary as needed, but may be between 25 and 50 mm. Each microchannel 72 is formed by a pair of spaced apart electrodes 74 and 76 defining two opposing lateral surfaces 78 and 80 of microchannel 72 (depicted as the top and bottom surfaces of a rectangular channel, but it could instead be the left and right sides). Electrodes 74 and 76 are wrapped with dielectric material 82 which protects against electric shocks and increases the service life of filter 54. Every adjacent electrode 74 and 76 is oppositely charged, so that each microchannel 72 has one lateral surface 78 having a positive or negative charge while the opposing lateral surface 80 has the opposite charge, thereby forming a strong electric field within the space 84 formed inside each microchannel 72. The microchannel 72 utilizes 24 VDC to create the electric field. Charged air particles leaving field generator 52 after being charged by corona discharge 64 will pass into microchannels 72 and enter the strong electric field formed therein. Any charged particles will be arrested and firmly held by an oppositely charged internal lateral surface 78 or 80 of microchannels 72, as seen in FIGS. 7 and 8. Microchannels 72 of intense field dielectric filter 54 have relatively low resistance and thus produce a minor pressure drop in air flow of between 10 and 30 Pascals. Intense field dielectric filter 54 can provide an arresting capability of close to 100 percent for charged particles passing through microchannels 72. For example, an exemplary system configured for a single rail car can reduce the concentration of atmospheric particulate matter of 2.5 micrometers (PM 2.5) from 999 micrograms per cubic meter (ug/m$^3$) to 46 micrograms per cubic meter (ug/m$^3$). Pathogens such as bacteria that are carried by arrested particles can be trapped and destroyed by the high strength electrical field. Under normal loads, intense field dielectric filter 54 can be used for between eight and ten weeks before cleaning is needed. Even if intense field dielectric filter 54 is powered off, static electricity will remain in filter 54 for a long period of time to firmly lock any adsorbed dust on either of electrode 74 and 76. The dielectric filter 54 can be cleaned by using a vacuum with a brush attachment, and if necessary, a neutral cleaning agent and a soft brush and water.

Figure 9:
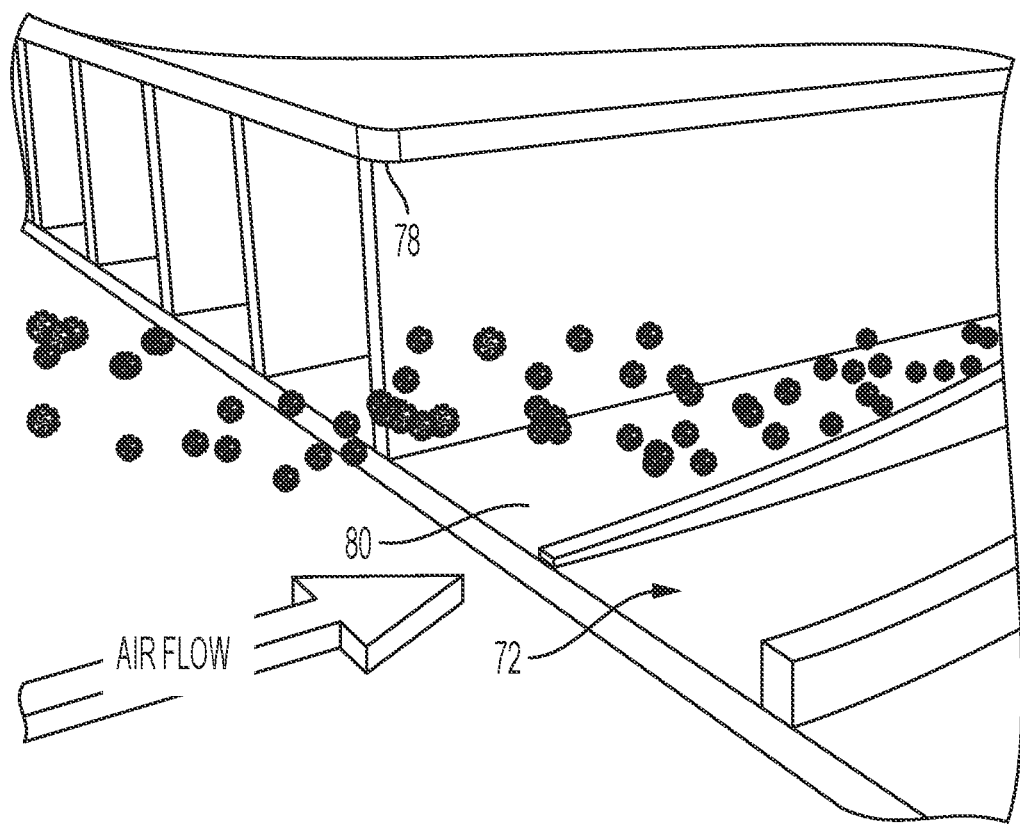
FIG. 9 is a perspective view of a microchannel of an intense field dielectric filter according to the present invention.

Referring to FIG. 9, ultraviolet germicidal irradiation phase 30 of air treatment system 10 comprises an ultraviolet germicidal irradiation (UVGI) unit 40 positioned to direct a therapeutic amount of UV light into any air passing through passageway 16. For example, UVGI unit may comprise an array of UV sources 42 and a reflector 44 to concentrate UV light in a predetermined direction. UVGI unit 40 preferably produces UVC wavelength light (250-260) nanometers as those wavelengths are well-established for disinfection of harmful pathogens such as bacteria and viruses. UV sources 42 may comprise conventional UV light bulbs or UVC emitting light emitting diodes (LEDs) that provide a predetermined dosage of UVC irradiation, typically measured in microwatts per centimeter squared (uW/cm$^2$). The UVGI unit ideally produces around 128,800 uW/cm$^2$ at 150 mm, 7 degrees Celsius and airflow of 2.5 meters per second, but could varied depending on application specific requirements. As UVGI unit 40 is contained with housing 12 and oriented to direct UVC light into passageway 16, there is minimal risk that passengers or general maintenance personnel will be exposed to UVC light during normal use. A safety switch or cutoff may be installed in the access port to interrupt power to UVGI unit 40 in case it is not manually powered off prior to maintenance. UVGI unit 40 may be configured to output enough UVC light to inactivate 85 percent or more of pathogens that may be suspended in the air flowing through passageway 16 in a single pass, and up to 99.9 percent in a multiple pass configuration. For example, depending on the air flow rate, UVC light having a peak a wavelength of between 250 and 260 nanometers can provide peak disinfection. As the efficacy of germicidal ultraviolet irradiation is the product of time and intensity, the intensity of the UVC light emitting from UVGI unit 40 can be designed according to the air flow rate and the amount of desired disinfection to provide acceptable disinfection even under worst case conditions, including temperature and germicidal efficacy of the bulbs at the end of their lifetime. The UVGI unit is powered of the low voltage power supply to be continuously energized and provide the maximum germicidal potential when the train power supply is active.

Figure 10:
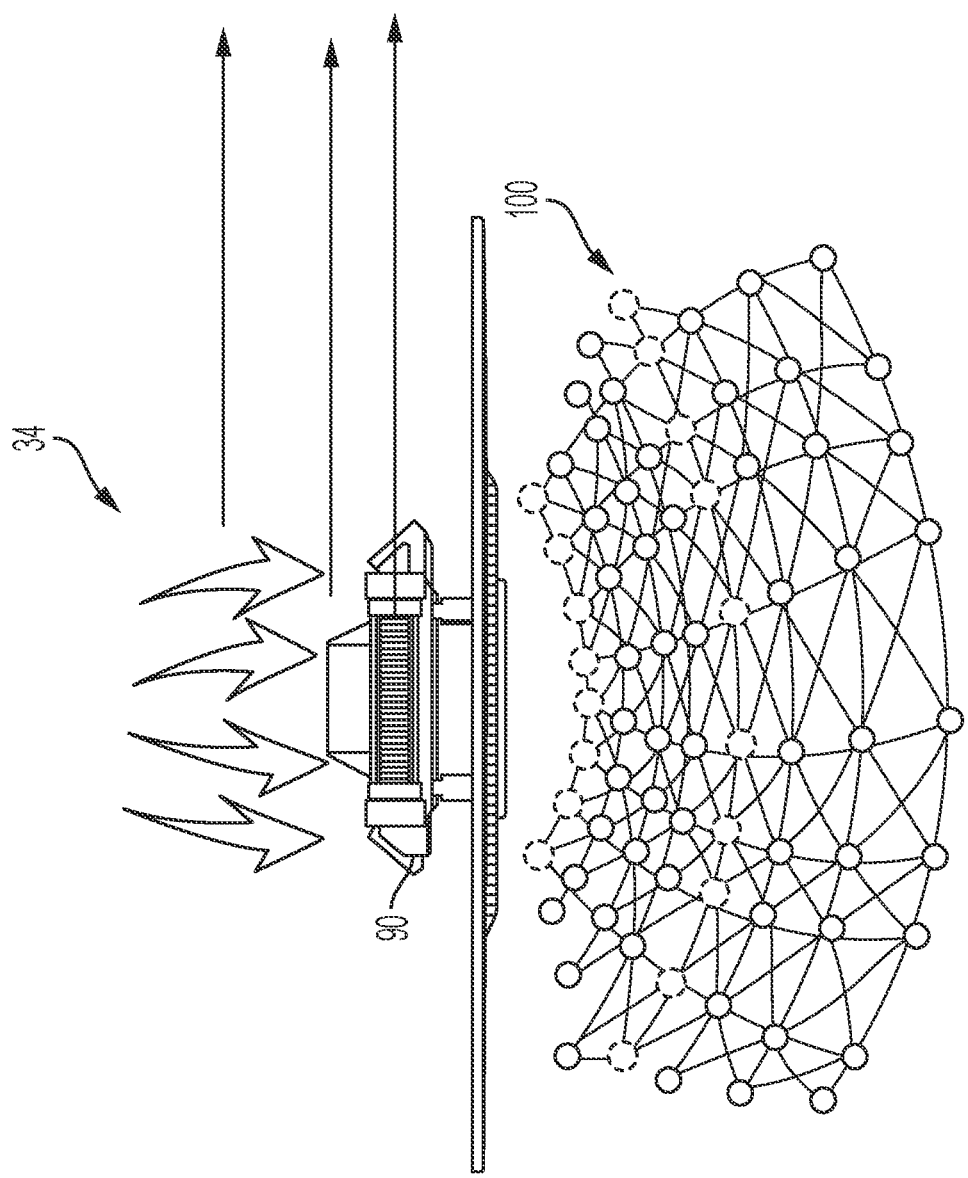
FIG. 10 is a schematic of dielectric barrier discharge phase of a rail car air treatment system according to the present invention.
Figure 11:
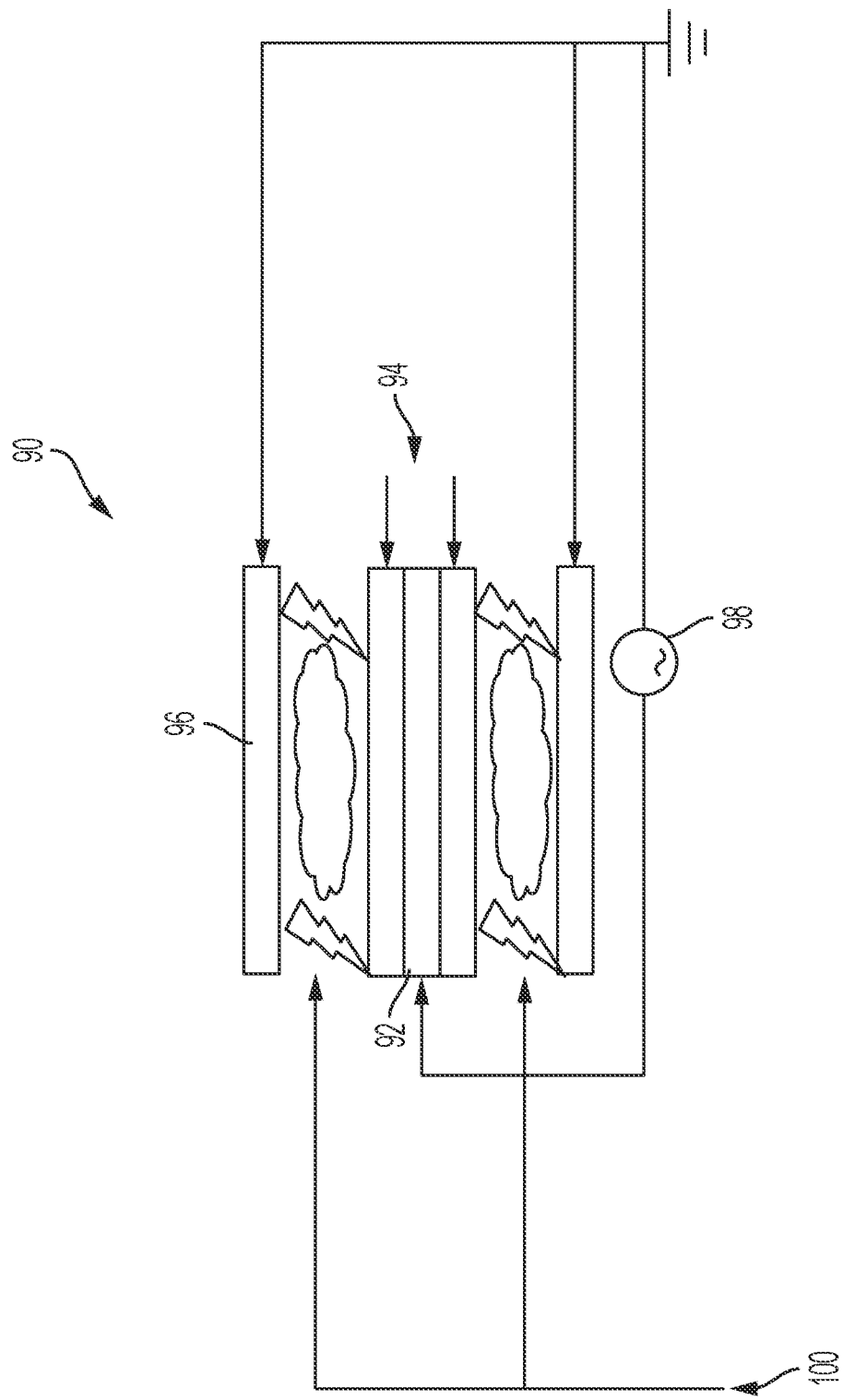
FIG. 11 is a schematic of an alternative arrangement for a dielectric barrier discharge unit according to the present invention.

Referring to FIGS. 10 and 11, dielectric barrier discharge phase 34 comprises a dielectric barrier discharge unit 90 having a high voltage discharge electrode 92 coupled to a dielectric barrier 94 and spaced apart from a ground electrode 96. When a high voltage AC generator 98, such as one operating at 2800 VAC, is coupled to high voltage discharge electrode 92 and ground electrode 96, a large quantity of positive and negative oxygen ions are generated in the chamber 100 between high voltage discharge electrode 92 and ground electrode 96. Dielectric barrier discharge unit 90 thus produces a bi-polar ionized gas discharge in the discharge chamber 100. Dielectric barrier 94 can cover the electrode or be suspended in the discharge space 84. When a sufficiently high AC voltage is applied to discharge electrode 92, such as at 2800 VAC, the gas between the electrodes 92 and 96 will be broken down at a very high gas pressure to form what is referred to as a dielectric barrier discharge or low temperature plasma. By systematically controlling the electrode structure and discharge parameters, dielectric barrier discharge unit 90 can carry out discharge work in a relatively low voltage and produce free electrons with high potential and kinetic energy. In the discharge space 84, the atoms in the molecules gain enough kinetic energy to separate from each other or dissociate, with the outer electrons of atoms becoming free to produce ions. For example, dielectric barrier discharge unit 90 operating at 5 Watts can generate 3.5 to 5 million ions per cubic centimeter ($cm^3$) for comprehensive and continuous purification without any secondary pollution i.e. no ozone is produced. The ions will attach to and break down any pathogens in the air, such as bacteria and viruses, as well as any chemicals, such as formaldehyde, TVOC, ammonia, and cigarette smoke residue. The ions additionally attach to small particulate matter which results in the coagulation of them due to charge polarity, resulting in increased weight and particulate dust dropping from the air. The ionic disinfection provided by dielectric barrier discharge phase 34 may continue as air leaves housing 12 and is passed through duct work and the rail car compartment including the surfaces within. Maintenance of dielectric barrier discharge phase 34 is limited to brushing of the surface periodic (three to six month intervals) to remove any accumulated dust.

System 10 may further comprise a local controller programmed to dynamically operate any one or more of intense field dielectric phase 32, ultraviolet germicidal irradiation phase 30, and dielectric barrier discharge phase 34 according to current conditions. For example, it may be possible to determine the passenger loading for the rail car in which system 10 is installed using carbon dioxide sensor, vision based person counting, etc., and then operate system 10 based on the real-time demands on the rail car so that system 10 is operated at maximum efficiency to ensure adequate air purification while reducing power consumption, extending the lifespan of the components, and maximizing service intervals. In addition, visual indicators may be used to indicate to passengers and/or maintenance personal the status of system 10, such as whether air purification is active and fully operational.

Ultraviolet germicidal irradiation phase 30, intense field dielectric phase 32, and a dielectric barrier discharge phase 34 thus work harmoniously to provide germicidal irradiation, physical filtration to remove particles and reduce virus transmission, and disinfection through the release of disinfection factors (positive and negative oxygen ions). The solution of the present invention thus can effectively reduce the infection risk and range of a pathogen such as a virus, while also serving as a mechanism for vehicle disinfection after the rail car returns to a maintenance or storage location.

The synergistic effects of the combination of ultraviolet germicidal irradiation phase 30, intense field dielectric phase 32, and a dielectric barrier discharge phase 34 of system 10 were evaluated and demonstrated with respect to removing/eliminating aerosolized MS2 Bacteriophage ATCC 15597-B1, as well as *E. coli* ATCC K-12. The efficiency of the device in an aerosol test study was evaluated to determine the effectiveness of the device to eliminate COVID-19 from within the recirculated air of rail vehicles to improve passenger and personnel safety. The efficacy of system 10 to eliminate aerosolized viruses in ISO 17025 accredited United States based laboratory testing in compliance with the EPA and FDA guidelines. Accordingly, two sets of testing were completed to validate the efficacy of system 10 to indicate personnel protection against COVID-19 and against other various viruses, bacteria, and hazardous airborne particulates.

In a first test, system 10 comprises a retro-modified railcar HVAC unit that integrated the blower fans and ultraviolet germicidal irradiation phase 30, intense field dielectric phase 32, and a dielectric barrier discharge phase 34, with a text box and cabling for actuation of the individual subsystems. The unit included recirculated and supply air sections to demonstrate system 10 integrated into a baseline representative model. System 10 was tested using 15, 30 and 60 minute contact times with the MS2 bacteriophage ATCC 15597-B1. A first set of testing at the longer contact times was intended to provide validation results in a comparable format with other products, which were tested under similar parameters. Six total test runs were performed in single replicate for device runs and triple replicate aerosolized sample collection to evaluate efficacy to remove/inactivate the MS2 bacteriophage ATCC 15597-B1 from the air, including a control run and various combinations of the devices.

The MS2 was first inoculated and then aerosolized into the test chamber via nebulizers for 60 minutes to reach appropriate concentration, then baseline samples were taken at t=0 min, and additional samples were then taken at t=15 min, t=30 min, and t=60 min. After the samples were collected, they were plated and incubated and then enumerated to determine microbial concentration. Additional testing at shorter contact times was carried out using the MS2 and *E. Coli* in single replicate sampling at 1, 3, and 5 minutes. In total, 6 test runs were performed again under a similar process as described above.

The testing was performed with MS2 Bacteriophage, which is a small, non-enveloped virus that is recognized by the EPA as one of the most difficult type of viruses to inactivate and therefore considered by the EPA to be a representative viral screening tool. Specifically, there is a hierarchy that is generally applied to categorize these, which includes: (1) Small, non-enveloped viruses—most difficult to inactivate (MS2 Bacteriophage fits in this categorization) e.g. poliovirus, enterovirus, or rhinovirus; (2) Large, non-enveloped viruses—moderately difficult to inactivate e.g. adenovirus, rotavirus, or papillomavirus; and (3) Enveloped viruses—easy to inactivate (COVID-19 fits this categorization) e.g. influenza, herpes virus, or hepatitis virus.

For all runs, 0.5 ml of MS2 bacteriophage ATCC 15597-B1 stock and 10.0 ml of *E. coli* ATCC K-12 culture were added to 34.5 ml of Phosphate Buffered Saline and mixed until homogeneous. 20.0 ml of inoculum was added to each nebulizer. MS2 virions are 23-28 nm in diameter and non-enveloped, compared to the COVID-19 virus, which is 60-140 nm in diameter and enveloped. Therefore, it is harder to capture the MS2, more difficult to irradiate in terms of surface area, and requires significantly more radiation to inactivate. On this predication of the testing and its relevance for the intended application, the results presented can be construed to represent the minimum efficacy against COVID-19 and other flu-like viruses.

Air samples were taken in single replicate at the following time points after the device was running: 1 minute, 3 minutes and 5 minutes. Device was turned off after 5 minutes of total treatment time and samplers were allowed to continue sampling. Test microorganisms were grown on appropriate media. Cultures used for test inoculum are evaluated for sterility, washed and concentrated in sterile phosphate buffered saline upon harvesting. The test inoculum was split into two equal parts and added to the appropriate number of nebulizers. Liquid culture did not exceed 20 ml per nebulizer. The device was setup per protocol requirements and operated per manufacturer's instructions. The chamber is setup and the safety checklist was completed prior to test initiation. Test was initiated by aerosolizing the microorganisms per the nebulizers and allowing the concentration to reach the required $PFU/m^3$. Once the concentration was reached, a time zero sample was taken, then the device was operated for the specified contact time and an additional sample was taken for each contact time. A decontamination process was run, 4 hours of UV exposure, prior to any humans entering the testing chamber. Samples were enumerated using standard dilution and plating techniques. Microbial concentrations were determined after appropriate incubation times. Reductions of microorganisms are calculated relative to concentration of the time zero or corresponding control run sample as applicable.

System 10 achieved a significant reduction in the aerosolized virus in a very short time interval. After just five minutes, the system reaches 99.98%, which is approximately a sanitation level equivalent to using standard hand sanitizer (99.99%). At 15 minutes, system 10 achieved a 99.99993% elimination of virus, approaching sterilization levels as it is increasing to a >99.99998% reduction after 30 minutes, and continuing >99.99998% through the 60-minute test period. Additional testing was performed as *E. Coli* at the shorter contact times to provide another live microorganism example to demonstrate the efficacy against bacterium. The system reached up to 99.998% efficacy as soon as one minute. The result demonstrate that system 10 acts to filter and purify the air and is effective not only on the immediate threat of the COVID-19 virus but that it will provide the same level of protection against other virus that recur annually in cold and flu season.

Table 1 below provides the test results for MS2 Bacteriophage ATCC 15597-B1 and system 10.

TABLE 1

| Time (mins) | Average $PFU/m^3$ | Percent Reduction Compared to Time Zero | Adjusted Percent Reduction[2] Compared to Baseline | $Log_{10}$ Reduction Compared to Time Zero[1] | Adjusted $Log_{10}$ Reduction[1] Compared to Baseline |
|---|---|---|---|---|---|
| 0 | 6.32E+08 | N/A | N/A | N/A | N/A |
| 15 | 4.64E+02 | 99.99993% | 13.196% | 6.13 | 5.25 |
| 30 | <1.47E+02 | >99.99998% | >11.797% | >6.63 | >5.70 |
| 60 | <1.20E+02 | >99.99998% | >4.996% | >6.72 | >5.42 |

The limit of detection for this assay is 8.00 + 01 $PFU/m^3$ and values below the limit of detection are noted as "<8.00E+01" in the data table.
[1]The Log reductions for the Test Runs are adjusted to account for natural die-off and gravitational settling observed in the Control Run.
[2]The Percent reductions for the Test Runs are adjusted to account for the natural die-off and gravitational settling observed in the Control Run.

Table 2 below provides the detailed test results for MS2 Bacteriophage ATCC 15597-B1 and system 10 with shorted contact times:

TABLE 2

| Time (mins) | $PFU/m^3$ | Percent Reduction Compared to Time Zero | $Log_{10}$ Reduction Compared to Time Zero | Adjusted $Log_{10}$ Reduction[1] to Baseline |
|---|---|---|---|---|
| 0 | 6.32E+08 | N/A | N/A | N/A |
| 1 | 2.58E+06 | 99.59% | 2.39 | 2.21 |
| 3 | 3.94E+05 | 99.94% | 3.20 | 3.14 |
| 5 | 1.32E+05 | 99.98% | 3.68 | 3.50 |

The limit of detection for this assay is 8.00 + 01 $PFU/m^3$ and values below the limit of detection are noted as "<8.00E+01" in the data table.
[1]The Log reductions for the Test Runs are adjusted to account for natural die-off and gravitational settling observed in the Control Run.

Table 2 below provides the detailed test results for *E. coli* ATCC K-12 and system 10.

TABLE 2

| Time (mins) | $CFU/m^3$ | Percent Reduction Compared to Time Zero | Adjusted Percent Reduction[2] Compared to Baseline | $Log_{10}$ Reduction Compared to Time Zero[1] | Adjusted $Log_{10}$ Reduction[1] Compared to Baseline |
|---|---|---|---|---|---|
| 0 | 1.10E+06 | N/A | N/A | N/A | N/A |
| 1 | 8.96E+01 | 99.99993% | 99.992% | 4.09 | 3.97 |
| 3 | <8.96E+01 | >99.99998% | >99.992% | >4.09 | >4.01 |
| 5 | <8.64E+01 | >99.99998% | >99.992% | >4.11 | >3.92 |

The limit of detection for this assay is 8.00 + 01 $PFU/m^3$ and values below the limit of detection are noted as "<8.00E+01" in the data table.
[1]The Log reductions for the Test Runs are adjusted to account for natural die-off and gravitational settling observed in the Control Run.
[2]The Percent reductions for the Test Runs are adjusted to account for the natural die-off and gravitational settling observed in the Control Run.

By deploying system 10, rail operators will be able to reduce intense cleaning regimes that have been put in place and provide an independently validated filtration and purification system that will begin to restore confidence and encourage the travelling public to use public transport.

What is claimed is:

1. An air purification system for a rail car, comprising:
   a housing having an inlet, and an outlet, and a passageway extending between the inlet and the outlet to define an air flow pathway;
   a field generator having a series of openings formed therethrough and a series of electrodes, each of which is positioned in one of the series of openings so that a tip of each electrode extends into a center of each opening respectively;
   a field dielectric filter having a plurality of channels formed therethrough and aligned with the openings of the field generator, wherein each channel is defined by a first surface comprising a first electrode and a second surface opposing the first electrode and comprising a second electrode, wherein the first electrode and the second electrode are encompassed by a dielectric material;
   an ultraviolet radiation source positioned to direct ultraviolet illumination into the passageway; and
   a dielectric barrier discharge unit having a high voltage electrode that is coupled to a dielectric barrier, a ground electrode spaced apart from the high voltage electrode to define a plasma chamber, wherein the plasma chamber is in communication with the passageway.

2. The air purification system of claim 1, wherein the field generator is positioned transversely across the passageway so that the series of openings are positioned in the air flow pathway such that any air flowing through the air flow pathway will pass through the series of openings.

3. The air purification system of claim 2, further comprising a first power source coupled to the field generator to apply a first voltage to the tip of each electrode and to an edge of each opening that is sufficient to create a corona discharge therebetween.

4. The air purification system of claim 3, wherein the voltage applied to the tip of each electrode and an edge of each opening is about 8000 volts of direct current.

5. The air purification system of claim 4, further comprising a second power source coupled to the field dielectric filter to apply a second voltage to the first electrode and the second electrode.

6. The air purification system of claim 5, wherein the second voltage is 24 volts of direct current.

7. The air purification system of claim 6, wherein the field dielectric filter is positioned transversely across the passageway so that the channels are aligned with the air flow path.

8. The air purification system of claim 7, wherein the field dielectric filter is positioned transversely across the passageway so that the channels are aligned with the air flow path.

9. The air purification system of claim 8, wherein the channels are configured to result in a pressure drop in the air flow path of less than about 30 Pascals.

10. The air purification system of claim 9, wherein the plurality of channels are capable of reducing the amount of 2.5 micrometer sized particulates in the air flow path to about 46 micrograms per cubic meter.

11. The air purification system of claim 1, wherein the ultraviolet radiation source is configured to emit ultraviolet illumination having a wavelength of between 250 and 260 nanometers.

12. The air purification system of claim 11, wherein the ultraviolet radiation source produces around 128,800 microwatts per centimeter squared.

13. The air purification system of claim 1, further comprising a power source coupled to the high voltage electrode of the dielectric barrier discharge unit.

14. The air purification system of claim 13, wherein the power source supplies 2800 volts of alternating current to the high voltage electrode.

15. The air purification system of claim 14, wherein the dielectric barrier discharge unit is configured to discharge between 3.5 and 5 million ions per cubic centimeter into the air flow path.

* * * * *